United States Patent
Torrie (12)

(10) Patent No.: US 6,187,011 B1
(45) Date of Patent: Feb. 13, 2001

(54) POSITIONING A TIBIAL TUNNEL

(75) Inventor: Paul A. Torrie, Marblehead, MA (US)

(73) Assignee: Smith & Nephew, Inc., Andover, MA (US)

(*) Notice: Under 35 U.S.C. 154(b), the term of this patent shall be extended for 0 days.

(21) Appl. No.: 09/395,223

(22) Filed: Sep. 14, 1999

Related U.S. Application Data

(62) Division of application No. 08/985,684, filed on Dec. 5, 1997, now Pat. No. 5,968,050.

(51) Int. Cl.[7] ..................................................... A61B 17/56
(52) U.S. Cl. ................................ 606/96; 606/98; 606/104
(58) Field of Search .............................. 606/86, 87, 89, 606/73, 96, 102, 103, 104

(56) References Cited

U.S. PATENT DOCUMENTS

| | | |
|---|---|---|
| 4,535,768 | 8/1985 | Hourahane et al. . |
| 4,672,957 | 6/1987 | Hourahane . |

(List continued on next page.)

FOREIGN PATENT DOCUMENTS

| | | |
|---|---|---|
| 31 49 717 C1 | 7/1983 | (DE) . |
| 0350780 | 1/1990 | (EP) . |
| 0 556 500 A1 | 8/1993 | (EP) . |
| 0 715 832 A2 | 6/1996 | (EP) . |
| 2 700 465 | 1/1993 | (FR) . |
| 2 716 364 | 2/1994 | (FR) . |
| 92/00773 | 1/1992 | (WO) . |
| WO 95/19141 | 7/1995 | (WO) . |

OTHER PUBLICATIONS

DePuy, pamphlet, The first system with the features surgeons ask for.*

Dyonics, pamphlet, "Vector II Guide to the Knee Set", Jul. 1, 1987.

Acufex, pamphlet, "The Intra–Articular Measuring Device Created by ACUFEX is the Solution to Graft Tunnel Mismatch," Cat. No. 013199 (1994).

DePuy ProSource, pamphlet, Frontier ACL Reconstruction Guide System (1996).

Howell et al., "Serial Magnetic Resonance Study Assessing the Effects of Impingement on the MR Image of the Patellar Tendon Graft," Arthroscopy 8(3):350–358, Raven Press (1992).

Linvatec, Paramax ACL Guide System, 1994 Product Catalog.

Marzo et al., "Intraarticular Fibrous Nodule as a Cause of Loss of Extension Following Anterior Cruciate Ligament Reconstruction," Arthroscopy 8(1):10–18, Raven Press, Ltd. (1992).

Morgan et al., "Arthroscopic Meniscal Repair Evaluated by Second–Look Arthroscopy," The Amer. Journ. of Sports Medicine, vol. 19, No. 6 (1991), pp. 632–638.

Morgan et al., "The Tibial Insertion of the ACL—Where is It?," Delaware Orthopaedic Center et al., Scientific Exhibit, Hall D, SE 78 (abstract of ASJM 19(3):276–289, (1991).

Smith & Nephew, ordering information, Vector II Guide to the Knee System (1985).

*Primary Examiner*—Pedro Philogene
(74) *Attorney, Agent, or Firm*—Fish & Richardson, PC

(57) ABSTRACT

A guide for positioning a tibial tunnel in anterior cruciate ligament (ACL) reconstruction. The guide includes a guide arm and a drill sleeve connected to the guide arm. A distal tip of the guide arm is configured to contact a femoral surface, and a distal tip of the drill sleeve is configured to contact a tibial surface when the distal tip of the guide arm contacts the femoral surface.

17 Claims, 11 Drawing Sheets

U.S. PATENT DOCUMENTS

| | | | |
|---|---|---|---|
| 4,708,139 | * | 11/1987 | Dunbar, IV ................................ 606/96 |
| 4,739,751 | * | 4/1988 | Sapega et al. ........................... 606/73 |
| 4,781,182 | | 11/1988 | Purnell et al. .................... 128/92 VD |
| 4,813,407 | | 3/1989 | Vogen ................................ 128/92 VZ |
| 4,823,780 | | 4/1989 | Odensten et al. ................ 128/92 VD |
| 4,883,048 | | 11/1989 | Purnell et al. .................... 128/92 VD |
| 4,920,958 | | 5/1990 | Walt et al. . |
| 4,945,904 | | 8/1990 | Bolton et al. ............................ 606/96 |
| 4,952,213 | | 8/1990 | Bowman et al. ........................ 606/79 |
| 5,009,661 | | 4/1991 | Michelson ............................. 606/170 |
| 5,037,426 | * | 8/1991 | Goble et al. ............................ 606/96 |
| 5,112,335 | | 5/1992 | Laboureau et al. ..................... 606/88 |
| 5,112,337 | * | 5/1992 | Paulos et al. ........................... 606/96 |
| 5,139,520 | * | 8/1992 | Rosenberg ............................. 606/87 |
| 5,154,720 | * | 10/1992 | Trott et al. .............................. 606/96 |
| 5,163,940 | * | 11/1992 | Bourque ................................. 606/96 |
| 5,269,786 | | 12/1993 | Morgan . |
| 5,320,115 | | 6/1994 | Kenna . |
| 5,350,383 | | 9/1994 | Schmieding et al. . |
| 5,409,494 | | 4/1995 | Morgan . |
| 5,520,693 | | 5/1996 | McGuire et al. ....................... 606/86 |
| 5,562,664 | | 10/1996 | Durlacher et al. . |
| 5,562,669 | | 10/1996 | McGuire ................................ 606/72 |
| 5,613,971 | * | 3/1997 | Lower et al. ........................... 606/96 |
| 5,643,273 | * | 7/1997 | Clark ...................................... 606/96 |
| 5,681,320 | * | 10/1997 | McGuire ................................ 606/96 |
| 5,743,909 | * | 4/1998 | Collette .................................. 606/96 |

* cited by examiner

POSITIONING A TIBIAL TUNNEL

This application is a divisional of U.S. application Ser. No. 08/985,684, filed Dec. 5, 1997, now U.S. Pat. No. 5,968,050.

TECHNICAL FIELD

This invention relates to positioning a tibial tunnel in anterior cruciate ligament (ACL) reconstruction.

BACKGROUND INFORMATION

A damaged ACL is often replaced with a graft from a patellar tendon or a semitendinosus tendon. Generally, the patellar tendon graft has small bone pieces attached to its ends, whereas the semitendinosus tendon graft does not. Tunnels are formed in the tibia and femur for use in implanting the graft in the patient's knee. The graft is then secured in the tunnels by fixation means, such as, for example, interference screws or sutures tied to screw posts.

SUMMARY

This invention features a guide for positioning a tibial tunnel in anterior cruciate ligament (ACL) reconstruction.

In one general aspect of the invention, the guide includes a guide arm and a drill sleeve connected to the guide arm. A distal tip of the guide arm is configured to contact a femoral surface, and a distal tip of the drill sleeve is configured to contact a tibial surface when the distal tip of the guide arm contacts the femoral surface.

Embodiments may include one or more of the following features. For example, the guide may include a handle to which the guide arm and the drill sleeve may be connected, such that the guide arm and the drill sleeve are connected through their connections to the handle. The guide arm may be located at one end of the handle, and the drill sleeve may be located at an opposite end of the handle.

An orientation of the guide arm may be adjusted with respect to the drill sleeve. The guide arm may have markings for indicating the orientation of the guide arm with respect to the drill sleeve.

The drill sleeve may be configured to direct a guidewire into the tibial surface to locate the tibial tunnel. The drill sleeve may have markings for measuring the length of the tibial tunnel. The distal tip of the drill sleeve may include an angled opening surrounded by teeth.

The distal tip of the guide arm may include a hook configured to contact the femoral surface at, for example, the posterior cortex of the femoral notch. The guide arm may provide an offset from a point at which the distal tip contacts the femoral surface (e.g., the posterior cortex of the femoral notch) to a longitudinal axis of the drill sleeve (i.e., the axis of the tibial tunnel).

The distal tip of the guide arm also may include a spike configured to contact a tibial plateau. The size of the spike may vary depending on the desired ease of insertion of the guide arm. For example, the guide arm is easy to insert into the patient's knee when the spike is short.

In other embodiments, the guide arm may include a first distal arm portion having a hook configured to contact the femoral surface and a second distal arm portion having a spike configured to contact the tibial plateau. When the guide arm includes two distal arm portions, the guide may be adjusted to compensate for various femoral offsets and femoral notch heights.

The first distal arm portion may be configured to slide over the second distal arm portion. This permits adjustment of the guide to compensate for various femoral offsets. Alternatively, the first distal arm portion may be attached to the second distal arm portion by a spring. This permits adjustment of the guide to compensate for various femoral notch heights. In other embodiments, the first distal arm portion may be attached to the second distal arm portion by a linkage or at a pivot point. The guide arm is easy to insert into the patient's knee when the two distal arm portions are attached at a pivot point because the pivot point permits the spike to be deployed into the tibial plateau.

In other embodiments, the guide may include a device for indicating isometry. Isometry exists when the distance between the femoral tunnel opening and the tibial tunnel opening remains constant during extension of the knee. The device may be an isometry linkage. The length of the isometry linkage may be adjusted to compensate for various femoral notch heights by using hydraulic means or another extending mechanism. The device also may be an isometry mechanism located outside the patient's knee or an isometry suture.

Another general aspect of the invention features a method for positioning a tibial tunnel using the guide discussed above. In use, the guide is positioned in a patient's knee so that the distal tip of the drill sleeve contacts the tibial surface and the distal tip of the guide arm contacts a femoral surface (e.g., the posterior cortex of the femoral notch). Next, a guidewire is inserted through the drill sleeve and drilled through the tibia. The guide is removed from the patient's knee, leaving the guidewire in place to locate the tibial tunnel. Finally, a cannulated drill bit is placed over the guidewire for drilling the tibial tunnel.

Among other advantages, the invention provides an efficient and accurate way of positioning the tibial tunnel. For example, the guide references a bone surface (e.g., a femoral surface) for positioning the tibial tunnel, rather than a soft tissue surface. Moreover, the guide references a particular region of the femoral surface (e.g., the posterior cortex of the femoral notch) for positioning the tibial tunnel.

Other features and advantages of the invention will be apparent from the following detailed description, including the drawings, and from the claims.

DETAILED DESCRIPTION

Figure 1:
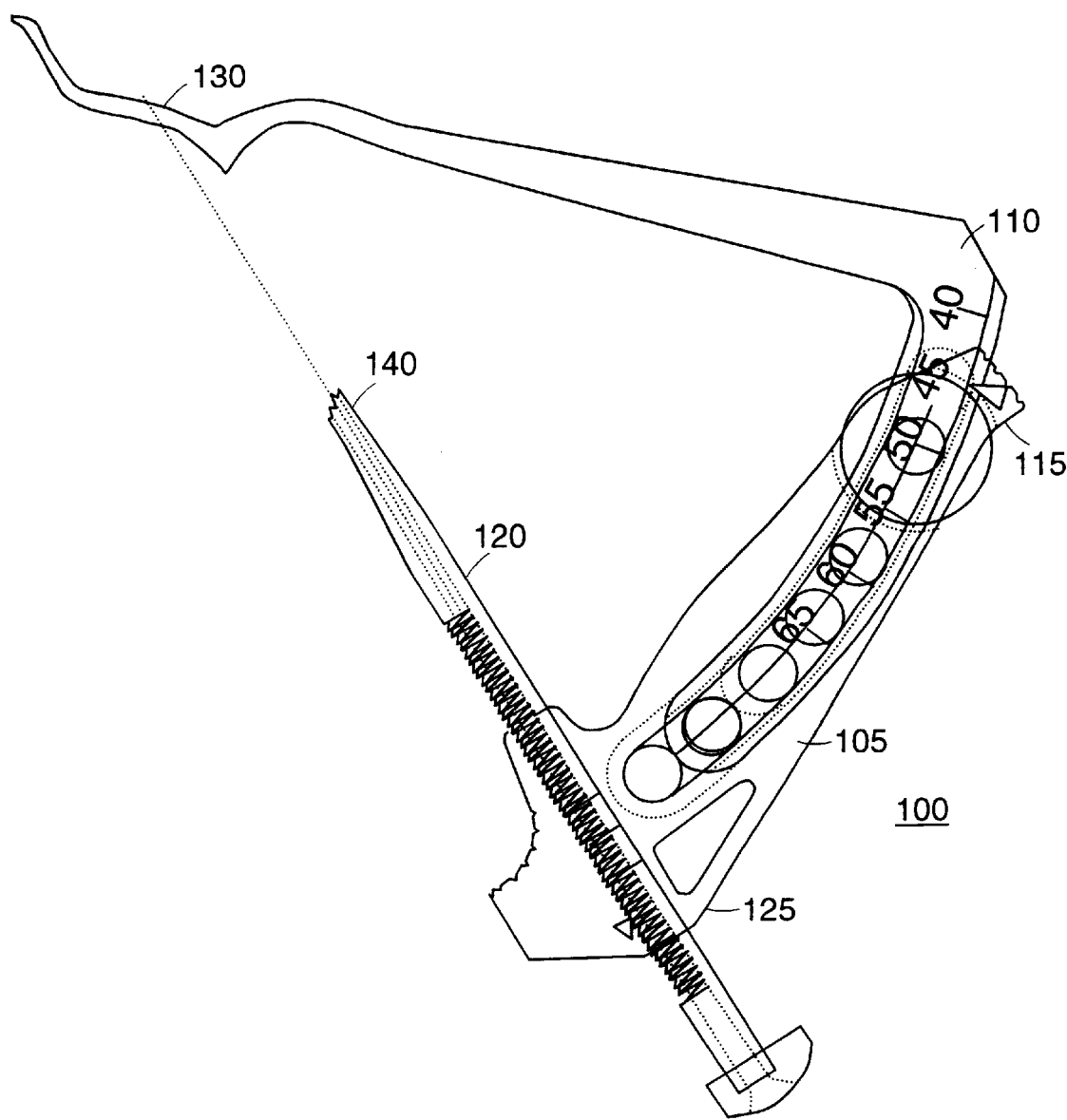
FIG. 1 is side view of a guide for positioning a tibial tunnel.

FIG. 1 shows a guide 100 for positioning a tibial tunnel in ACL reconstruction. Briefly, guide 100, which is described in detail below, includes a handle 105, a guide arm 110 located at one end 115 of handle 105, and a drill sleeve 120 (or "bullet") located at an opposite end 125 of handle 105. A distal tip 130 of guide arm 110 is configured to contact a femoral surface (e.g., the posterior cortex of the femoral notch), and a distal tip 140 of drill sleeve 120 is configured to contact a tibial surface (e.g., the anterior-medial surface of the tibia) when the distal tip 130 of the guide arm 110 contacts the femoral surface. Drill sleeve 120 is configured to direct a guidewire into the tibial surface to locate the tibial tunnel.

Figure 2A:
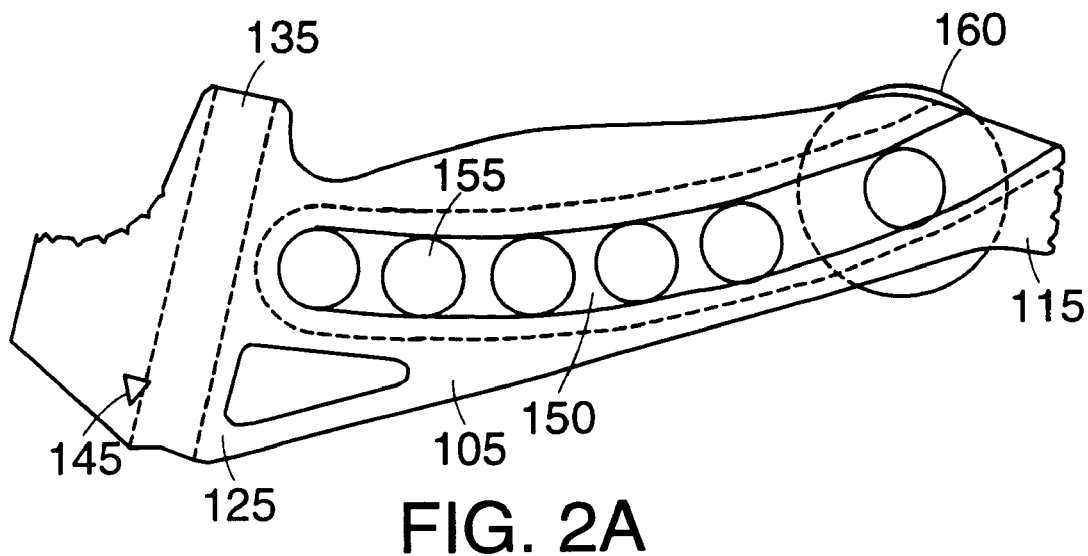
FIG. 2A is a side view of a handle of the guide of FIG. 1.
Figure 2B:
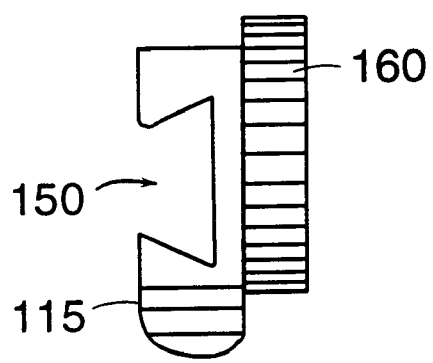
FIG. 2B is an end view of the handle of FIG. 2A.

Handle 105 is shown in detail in FIG. 2A. The exterior surface of handle 105 is curved so that the surgeon may easily grasp and manipulate guide 100 during surgery. Handle 105 has a cylindrical bore 135 at end 125. Bore 135 provides a passageway for drill sleeve 120. A one-way ratchet 145 is located on one side of bore 135. Ratchet 145 engages drill sleeve 120 and holds drill sleeve 120 in place within bore 135. Handle 105 also has an arc-shaped slot 150 extending from end 115. Openings 155 in the bottom of slot 150 make handle 105 lightweight. Openings 155 also ensure that handle 105 cools quickly after autoclaving. As shown in FIG. 2B, slot 150 has a dovetail cross-section.

Handle 105 also has a locking-nut 160 that engages guide arm 110 and holds guide arm 110 in place in slot 150. This permits the surgeon to adjust the orientation of guide arm 110 with respect to drill sleeve 120. For example, when locking-nut 160 is loosened, guide arm 110 is free to slide along slot 150.

Figure 3A:
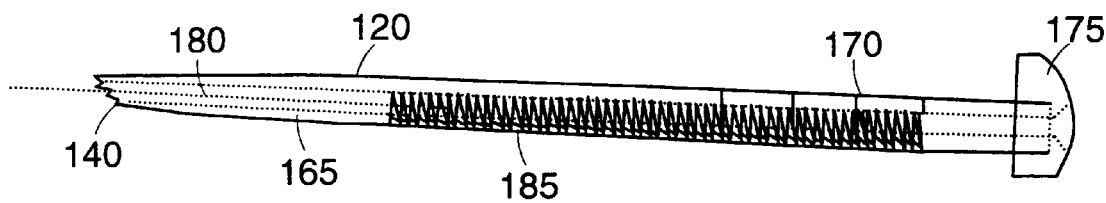
FIG. 3A is a side view of a drill sleeve of the guide of FIG. 1.

Drill sleeve 120 is sized for insertion through bore 135. As shown in detail in FIG. 3A, drill sleeve 120 has an elongated body 165, an angled distal tip 140, and a knob 175 at its proximal end. Body 165 has a cylindrical bore 180 that provides a passageway for a guidewire. Markings 170 (e.g., 20 mm, 30 mm, 40 mm) on the exterior of body 165 are used to measure the length of the tibial tunnel before drilling the guidewire through the tibia. Drill sleeve 120 also has ratchet teeth 185 along one side of body 165. One-way ratchet 145 of handle 105 engages ratchet teeth 185 on drill sleeve 120 and holds drill sleeve 120 in place within bore 135.

Drill sleeve 120 has a knob 175 at its proximal end so that the surgeon may easily grasp and manipulate drill sleeve 120 during surgery. Knob 175 is larger than the bore 135. Thus, when drill sleeve 120 is inserted through bore 135, knob 175 prevents drill sleeve 120 from being inserted completely through bore 135.

Figure 3B:
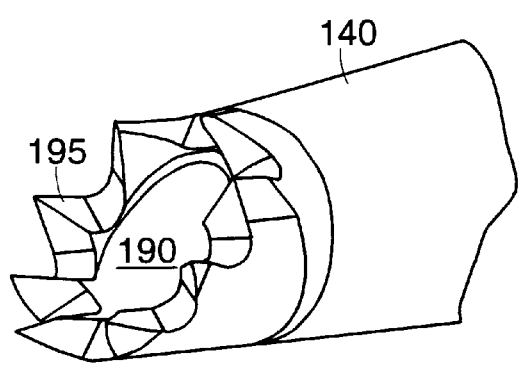
FIG. 3B is an enlarged perspective view of a distal tip of the drill sleeve of FIG. 3A.

As shown in detail in FIG. 3B, tip 140 has an angled opening 190 surrounded by teeth 195. When drill sleeve 120 is inserted through bore 135, tip 140 provides a stable engagement between drill sleeve 120 and the angled, anterior-medial surface of the tibia. Because angled opening 190 of tip 140 is flush against the angled tibial surface, teeth 195 fully contact the bone surface. Moreover, drill sleeve 120 supports the guidewire to the tibial surface to prevent the guidewire from being deflected by the hard bone surface. When the distal tip is not angled, there may be a gap between the teeth and the bone surface, which could result in deflection of the guidewire out of the drill sleeve through the gap.

Figure 4:
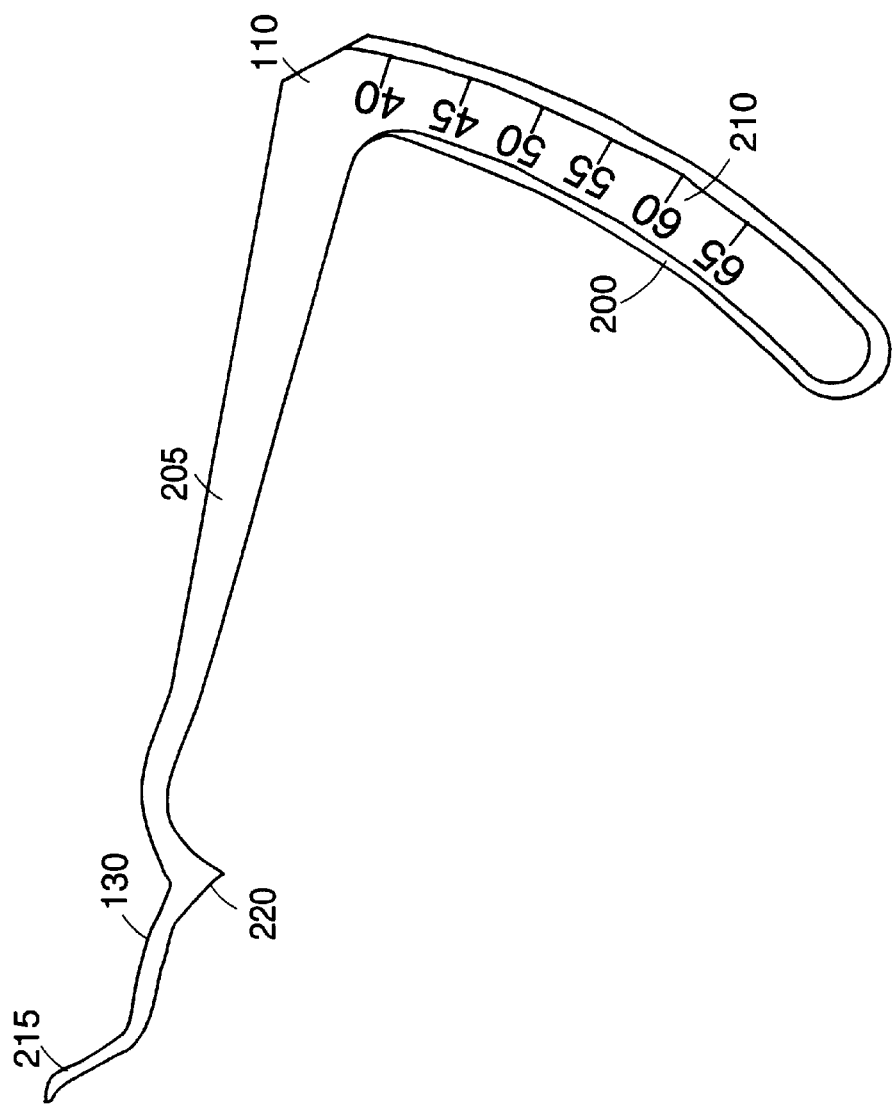
FIG. 4 is a side view of a guide arm of the guide of FIG. 1.

As shown in detail in FIG. 4, guide arm 110 has a proximal arm portion 200 and a distal arm portion 205. Proximal arm portion 200 is connected to handle 105 at end 115 and extends through slot 150. Proximal arm portion 200 is sized and shaped to fit in slot 150. For this reason, proximal arm portion 200 is arc-shaped and has a dovetail cross-section. The corresponding dovetail shapes of proximal arm portion 200 and slot 150 help to keep proximal arm portion 200 within slot 150. Proximal arm portion 200 also has markings 210 (e.g., 40°, 45°, 50°) for indicating the orientation of guide arm 110 with respect to drill sleeve 120.

Distal arm portion 205 has a distal tip 130 with a femoral cortex hook 215 and a spike 220. The size of spike 220 may vary depending on the desired ease of insertion of guide arm 110. For example, guide arm 110 is easy to insert into the patient's knee when spike 220 is short.

Figure 5:
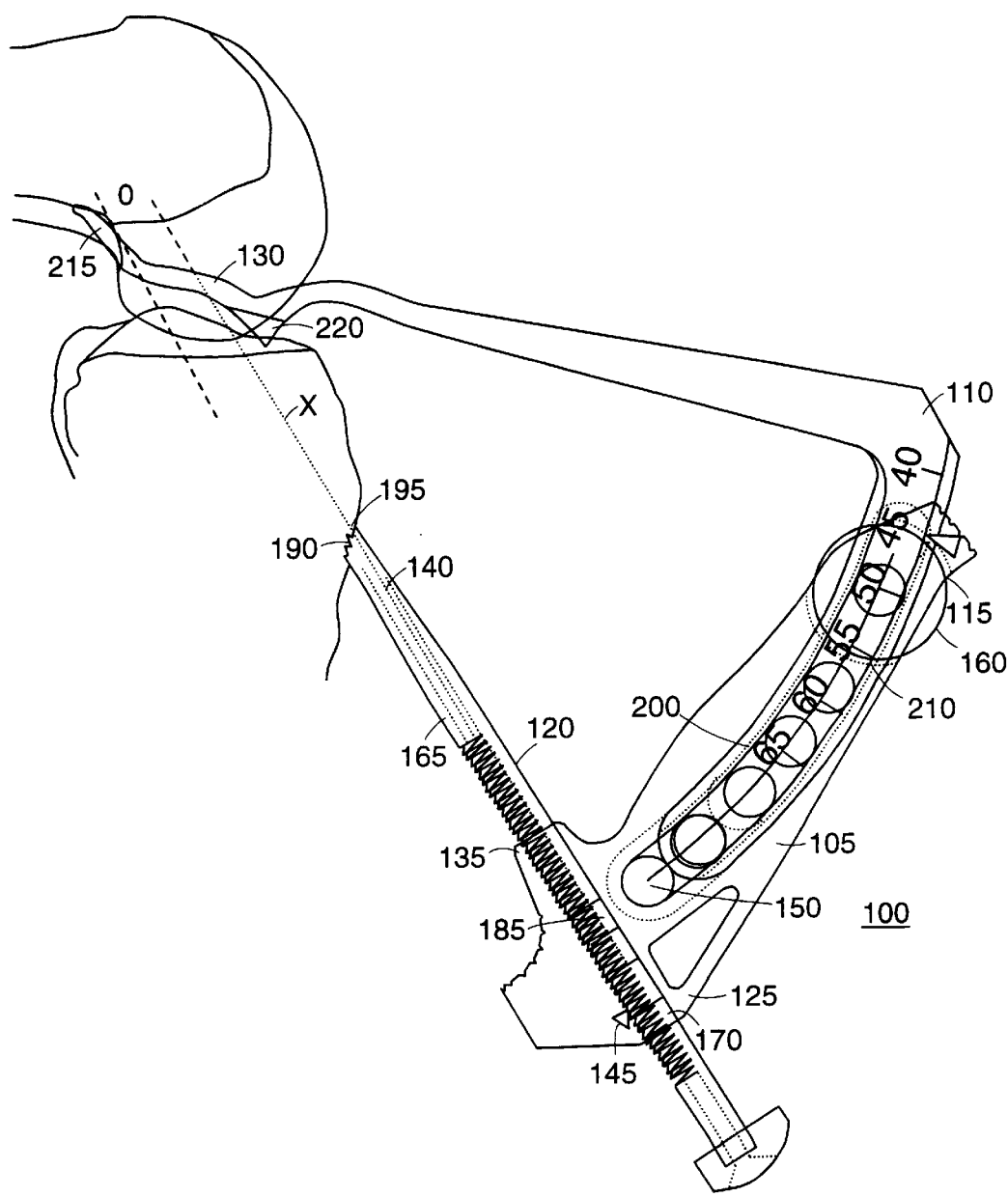
FIG. 5 is a side view of the guide of FIG. 1 positioned in a patient's knee.

The use of guide 100 will now be described with reference to FIG. 5. As noted above, guide 100 has a femoral offset guide arm 110. Generally, the femoral offset guide arm references a femoral surface, such as, for example, the posterior cortex of the femoral notch, for positioning the tibial tunnel. When guide 100 is positioned in the patient's knee, the femoral offset guide arm 110 provides an offset O from a point at which hook 215 contacts the femoral surface (e.g., the posterior cortex of the femoral notch) to the longitudinal axis X of drill sleeve 120 (i.e., the axis of the tibial tunnel).

The surgeon adjusts the orientation of guide arm 110 with respect to drill sleeve 120 by sliding proximal arm portion 200 along slot 150 of handle 105. For example, the orientation of guide arm 110 with respect to drill sleeve 120 may vary depending on whether the surgeon is using a patellar tendon graft or a semitendinosus tendon graft. Moreover, by adjusting the orientation of guide arm 110 with respect to drill sleeve 120, the surgeon may vary the length of the tibial tunnel to compensate for the length of the graft.

Markings 210 indicate the orientation of guide arm 110 with respect to drill sleeve 120. Guide arm 110 is positioned in the desired orientation by tightening locking-nut 160. Hook 215 at distal tip 130 of guide arm 110 is positioned against the posterior cortex of the femoral notch, and spike 220 is embedded in the anterior portion of the tibial plateau to hold guide arm 110 in place. Guide arm 110 is sized and shaped to provide an offset O from a point at which hook 215 contacts the femoral surface (e.g, the posterior cortex of the femoral notch) to the longitudinal axis X of drill sleeve 120 (i.e., the axis of the tibial tunnel).

Drill sleeve 120 is inserted through bore 135 of handle 105 so that angled opening 190 is flush against the angled, anterior-medial surface of the tibia, and teeth 195 fully contact the bone surface. Drill sleeve 120 is maintained within the bore 135 by one-way ratchet 145. Because drill sleeve 120 has ratchet teeth 185 along only one side of body 165, drill sleeve 120 may be adjusted within bore 135 by turning drill sleeve 120 such that ratchet teeth 185 no longer engage one-way ratchet 145.

Markings 170 are used to indicate the length of the tibial tunnel before drilling the guidewire. In particular, markings 170 measure the distance from angled opening 190 of drill sleeve 120 to a point at which the longitudinal axis X of drill sleeve 120 intersects the tibial plateau.

A guidewire (not shown) is inserted through drill sleeve 120 and drilled through the tibia. Because angled opening 190 is flush against the angled tibial surface, drill sleeve 120 supports the guidewire to the tibial surface to prevent the guidewire from being deflected by the hard bone surface. Guide 100 is then removed from the patient's knee, leaving the guidewire in place. Finally, a cannulated drill bit is placed over the guidewire for drilling the tibial tunnel.

Figure 6:
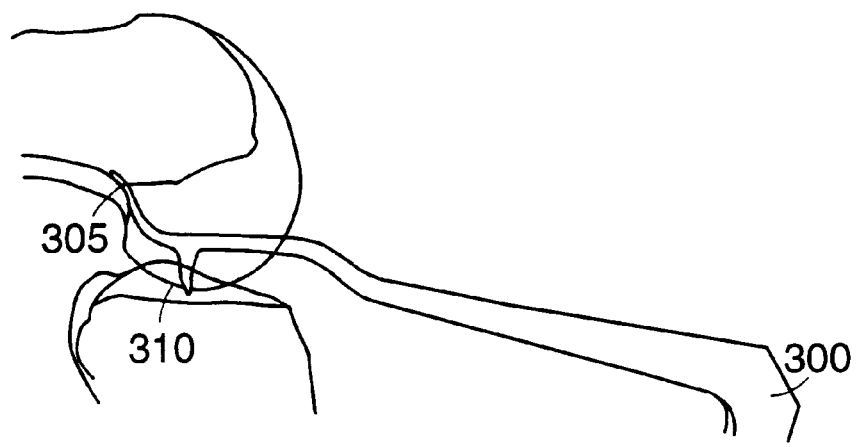
FIGS. 6–19 are side views of different embodiments of the guide arm.

FIGS. 6–19 show other embodiments of a femoral offset guide arm. In the embodiment shown in FIG. 6, guide arm 300 has a hook 305 and a spike 310. Spike 310 is long and thus, easy for the surgeon to see in the patient's knee. Spike 310 also may indicate where the guidewire will emerge from the tibial plateau, i.e., the location of the tibial tunnel opening.

Figure 7:
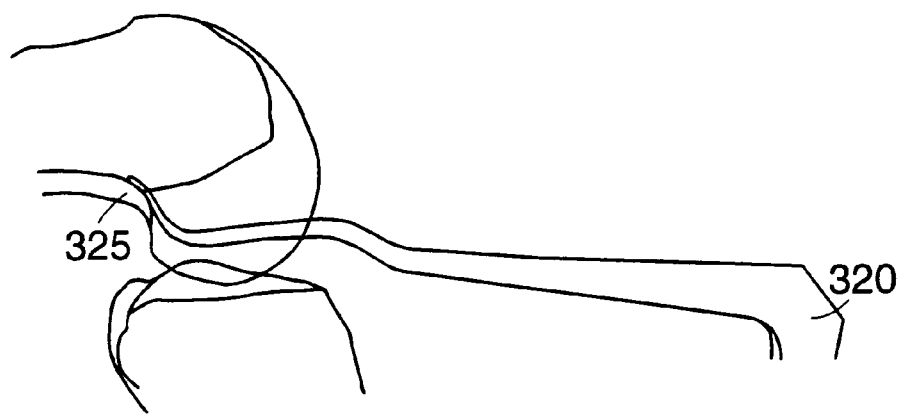

In the embodiment shown in FIG. 7, guide arm 320 has a hook 325, but no spike. Because guide arm 320 does not have a spike, guide arm 320 is easy to insert into the patient's knee, but must be held in place by the surgeon.

FIGS. 8–12 show other embodiments of the femoral offset guide arm (400a–400e), each of which has two distal arm portions: a distal spike arm portion (405a–405e) and a distal hook arm portion (410a–410e). Distal spike arm portion (405a–405e) has a spike (415a–415e) at its distal tip, and distal hook arm portion (410a–410e) has a femoral cortex hook (420a–420e) at its distal tip.

Figure 8:
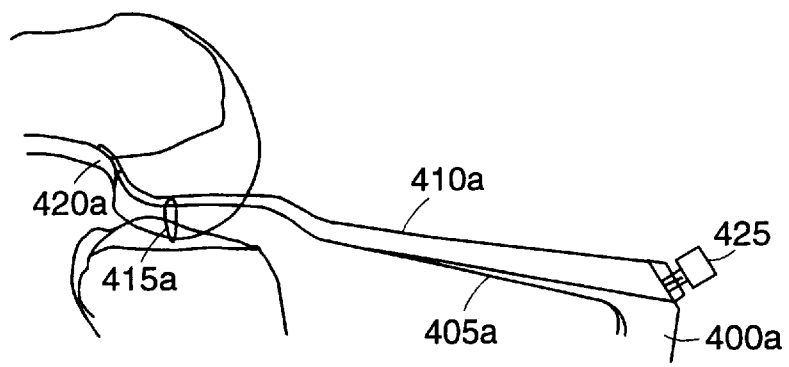

In FIG. 8, spike arm portion 405a is inserted into the patient's knee, and spike 415a is embedded into the tibial plateau. Hook 420a is then positioned against the posterior cortex of the femoral notch by sliding distal hook arm portion 410a over distal spike arm portion 405a. The position of distal hook arm portion 410a with respect to distal spike arm portion 405a may be adjusted by cam 425. Cam 425 also holds the distal hook arm portion 410a in place. Thus, guide arm 400a may be adjusted to compensate for various femoral offsets. Guide arm 400a is easy to insert into the patient's knee because distal hook arm portion 410a is not in place when distal spike arm portion 405a is inserted. If desired, however, the surgeon may insert distal spike arm portion 405a and distal hook arm portion 410a together into the patient's knee.

Figure 9:
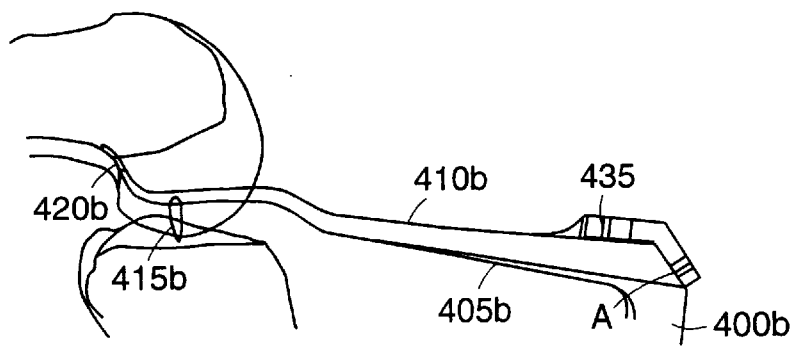

In FIG. 9, spike arm portion 405b is inserted into the patient's knee, and spike 415b is embedded into the tibial plateau. Hook 420b is positioned against the posterior cortex of the femoral notch by sliding distal hook arm portion 410b over distal spike arm portion 405b. Distal hook arm portion 410b is then connected to distal spike arm portion 405b at pivot point A. For example, distal hook arm portion 410b may be connected to distal spike arm portion 405b by use of male/female connectors or a pin. A spring 435 attached to the bottom of distal hook arm portion 410b pushes distal hook arm portion 410b against the femoral notch. Thus, guide arm 400b is adjusted to compensate for various femoral notch heights. Guide arm 400b is easy to insert into the patient's knee because distal hook arm portion 410b is not in place when distal spike arm portion 405b is inserted. If desired, however, the surgeon may insert distal spike arm portion 405b and distal hook arm portion 410b together into the patient's knee.

Figure 10:
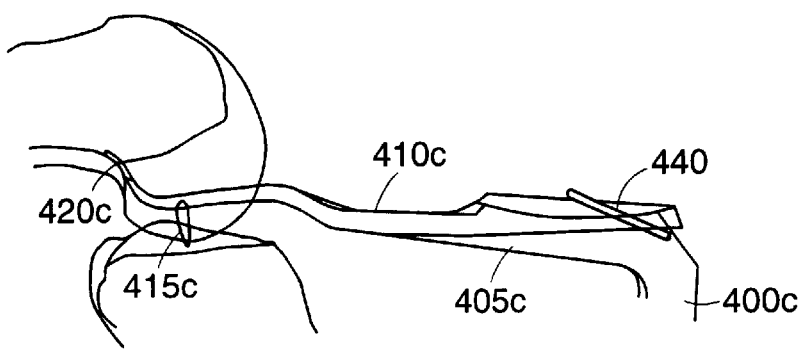

Referring to FIG. 10, guide arm 400c may be adjusted to compensate for various femoral notch heights. Spike arm portion 405c is inserted into the patient's knee, and spike 415c is embedded into the tibial plateau. Hook 420c is then positioned against the posterior cortex of the femoral notch by sliding distal hook arm portion 410c over distal spike arm portion 405c. A spring 440 attached to distal hook arm portion 410c and distal spike arm portion 405c pushes distal hook arm portion 410c against the femoral notch. Guide arm 400c is easy to insert into the patient's knee because distal hook arm portion 410c is not in place when distal spike arm portion 405c is inserted. If desired, however, the surgeon may insert distal spike arm portion 405c and distal hook arm portion 410c together into the patient's knee.

Figure 11:
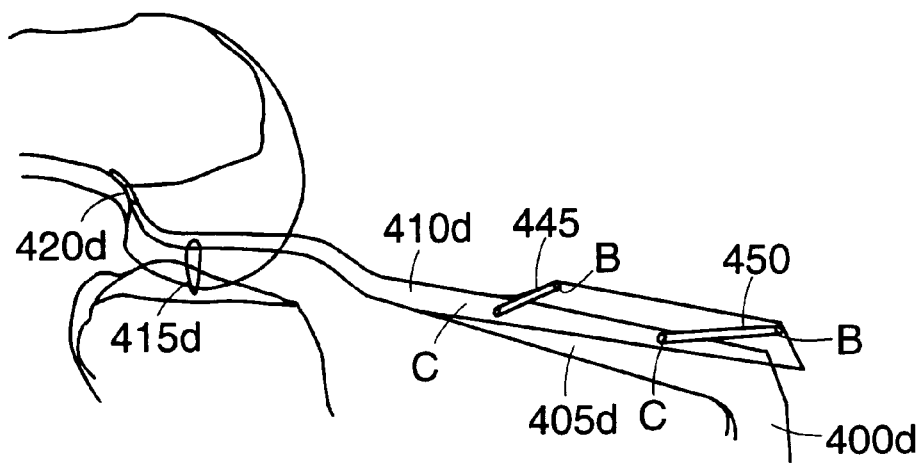

FIG. 11 shows another embodiment of a femoral offset guide arm that can be adjusted to compensate for various femoral notch heights. Distal hook arm portion 410d is attached to distal spike arm portion 405d by four bar linkages 445, 450, which are mounted in pairs on opposite sides of the guide arm. Linkages 445, 450 are attached to distal hook arm portion 410d at pivot points B and to distal spike arm portion 405d at pivot points C. Guide arm 400d is easy to insert into the patient's knee because distal hook arm portion 410d is not in place when distal spike arm portion 405d is inserted. If desired, however, the surgeon may insert distal spike arm portion 405d and distal hook arm portion 410d together into the patient's knee.

Figure 12:
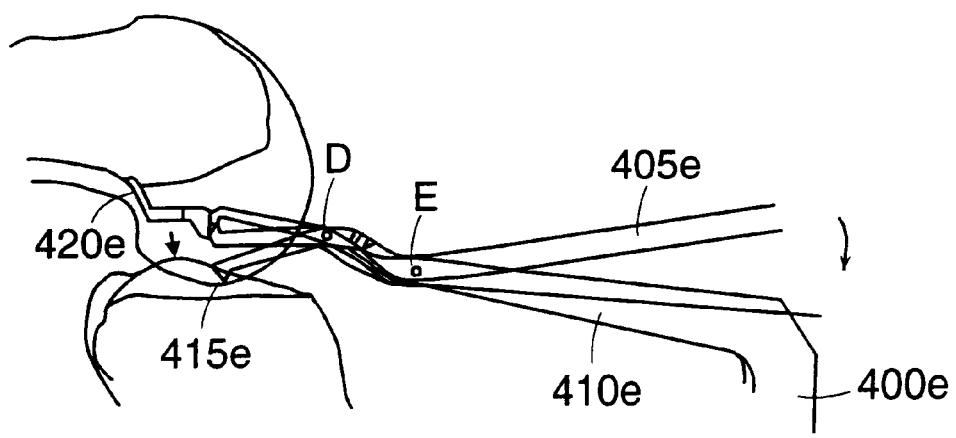

In FIG. 12, distal spike arm portion 405e is attached to distal hook arm portion 410e at two pivot points D and E. This permits alignment of spike 415e with hook 420e during insertion, so that guide arm 400e is easy to insert into the patient's knee. After hook 420e is positioned against the posterior cortex of the femoral notch, distal spike arm portion 405e is lowered, thereby embedding spike 415e in the tibial plateau.

Figure 13:
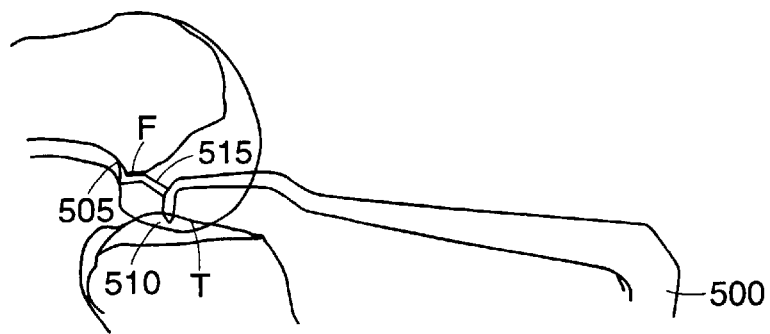

FIGS. 13–17 show embodiments of a femoral offset guide arm that can also be used to determine isometry. Isometry exists when the distance between the femoral tunnel opening F and tibial tunnel opening T remains constant during extension of the knee. In other words, the length of the graft remains constant during extension of the knee. Referring to FIG. 13, guide arm 500 has a femoral cortex hook 505 attached to a spike 510 by an isometry linkage 515. Isometry linkage 515 is movably attached to spike 510 and pivots around the tibial tunnel opening T. When hook 505 is positioned against the posterior cortex of the femoral notch, guide arm 500 may be adjusted by pivoting isometry linkage 515 around T. Isometry exists when spike 510 does not move during extension of the knee. Isometry linkage 515 is available in different lengths because the height of the femoral notch varies from patient to patient.

Figure 14:
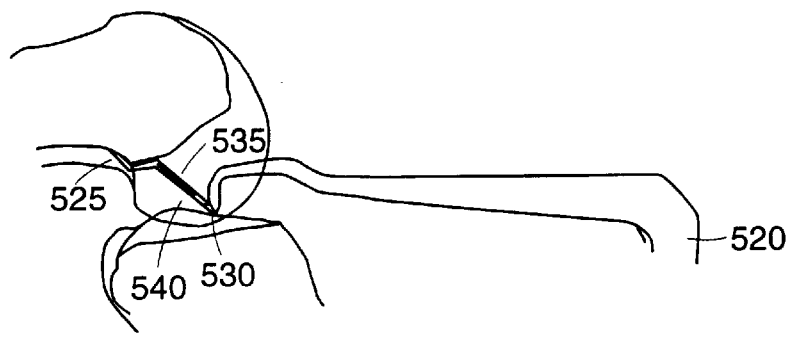

In FIG. 14, guide arm 520 has a femoral cortex hook 525 attached to a spike 530 by an adjustable isometry linkage 535. The length of isometry linkage 535 is controlled through hydraulic means 540. In this embodiment, isometry exists when the length of isometry linkage 535 remains constant during extension of the knee.

Figure 15:
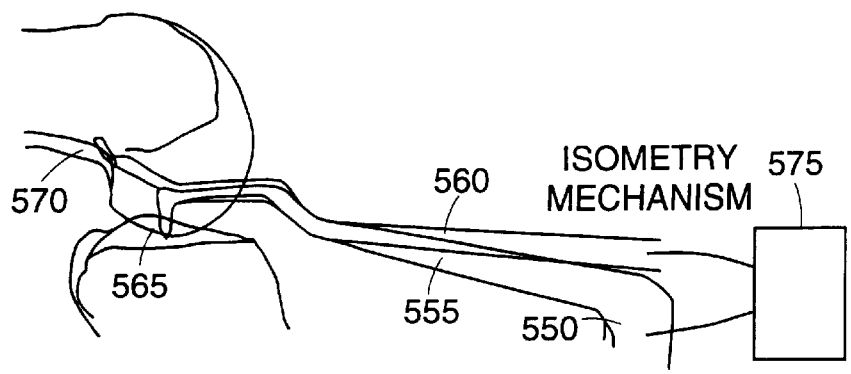

In FIG. 15, guide arm 550 has two distal arm portions: a distal spike arm portion 555 and a distal hook arm portion 560. Distal spike arm portion 555 has a spike 565 at its distal tip, and distal hook arm portion 560 has a femoral cortex hook 570 at its distal tip. An isometry mechanism 575 is connected to distal spike arm portion 555 and distal hook arm portion 560 and indicates any change in distance between hook 570 and spike 565 during extension of the knee. This isometry mechanism may be located outside the patient's knee. For example, isometry mechanism 575 could be a spring attached to a scale for measuring any change in distance between hook 570 and spike 565. Isometry exists when there is no change in distance between hook 570 and spike 565 during extension of the knee.

Figure 16:
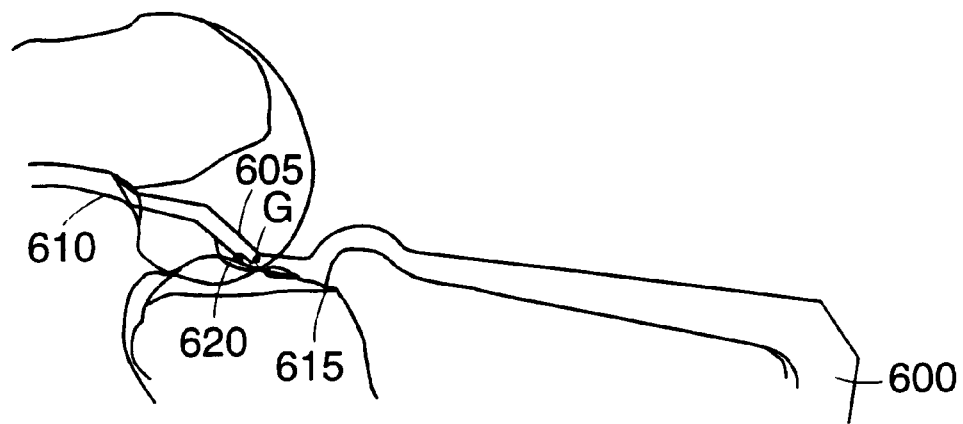

In the embodiment shown in FIG. 16, guide arm 600 has a distal tip 605 with a femoral cortex hook 610 attached to a spike 615 at pivot point G. A stop 620 limits the pivoting action of hook 610. Stop 620 also may include a spring (not shown) to push hook 610 against the femoral notch. The effective length of distal tip 605 may be adjusted by pivoting guide arm 600 around spike 615, thereby moving pivot point G either up or down. Isometry exists when pivot point G does not move during extension of the knee.

Figure 17:
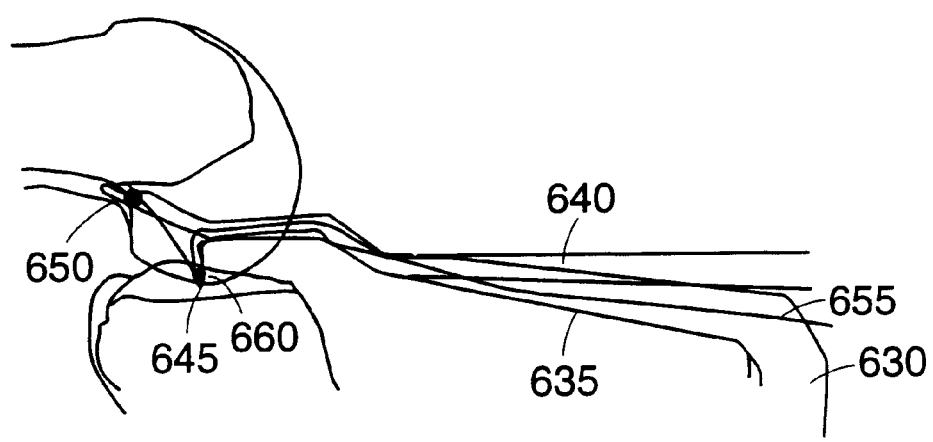

In FIG. 17, guide arm 630 has two distal arm portions: a distal spike arm portion 635 and a distal hook arm portion 640. Distal spike arm portion 635 has a spike 645 at its distal tip, and distal hook arm portion 640 has a femoral cortex hook 650 at its distal tip. Isometry suture 655 is connected to spike 645 and hook 650 using a pulley mechanism 660. Isometry suture 655 indicates any change in distance between the spike 645 and hook 650 during extension of the knee. Isometry exists when there is no suture movement.

Figure 18:
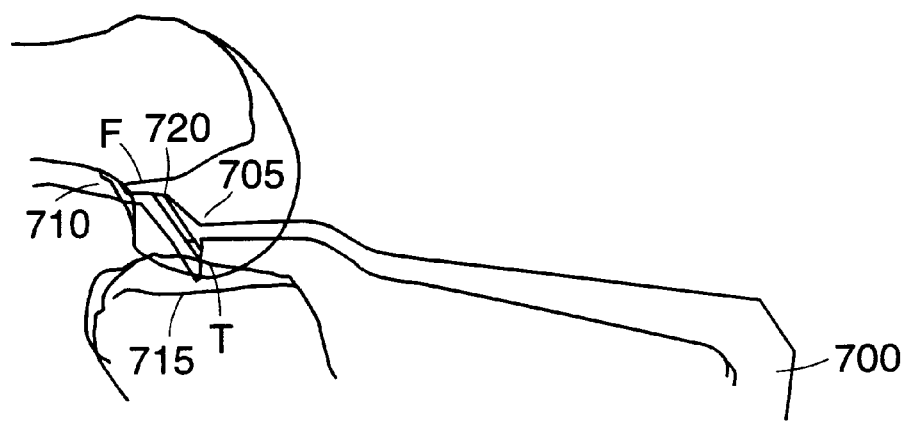

FIG. 18 shows another embodiment of a femoral offset guide arm. Guide arm 700 references the femur for positioning the tibial and femoral tunnels. In this embodiment, guide arm 700 has a distal tip 705 with a femoral cortex hook 710, a spike 715, and an S-shaped slot 720 for insertion of a guidewire. When the guidewire is drilled through the tibia, the guidewire exits the tibia at T, extends through slot 720, and enters the femur at F. Thus, slot 720 redirects the guidewire from the tibial tunnel opening T to the femoral tunnel opening F. Slot 720 extends to one side of distal tip 705 so that guide arm 700 may be removed from the patient's knee, leaving the guidewire in place. The guidewire locates the positions of the tibial and femoral tunnels.

Figure 19:
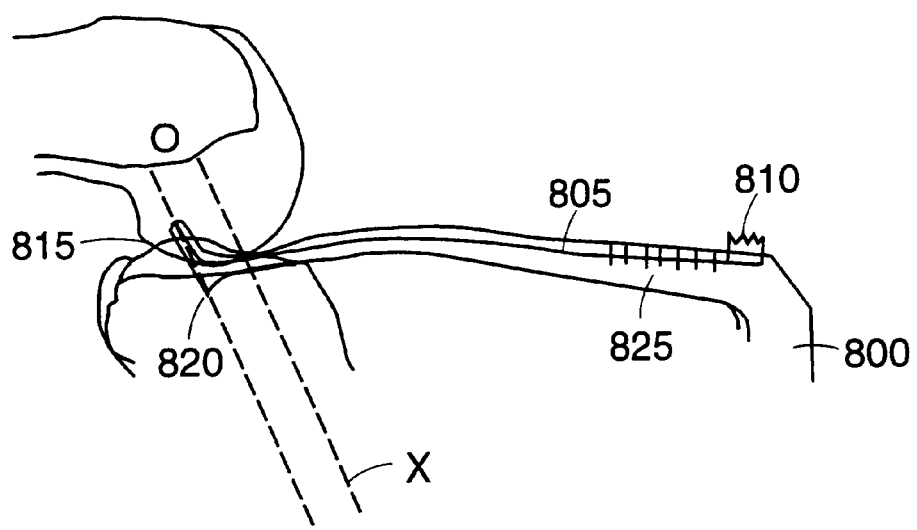

FIG. 19 shows another embodiment of a femoral offset guide arm. Generally, the femoral tunnel is positioned as posterior as possible on the femoral notch. Guide arm 800 references the posterior region of the femoral notch (e.g., the desired site of femoral tunnel opening) for positioning the tibial tunnel. Guide arm 800 provides an offset O from the reference point (e.g., the desired site of femoral tunnel opening) to the longitudinal axis X of drill sleeve 10 (i.e., the axis of the tibial tunnel). Guide arm 800 also measures the interarticular joint space or ACL length. Thus, the surgeon may adjust the length of the tibial tunnel to compensate for the length of the graft.

As shown in FIG. 19, guide arm 800 has a passageway for a wire 805 made from Nitinol or other high strain recovery material. Wire 805 is attached to a switch 810 and extends through or along guide arm 800 and out of distal tip 815. A spike 820 is embedded in the tibial plateau. In use, wire 805 is advanced out of distal tip 815 until wire 805 contacts the posterior region of the femoral notch at the desired site of the femoral tunnel opening. Markings 825 also indicate how much wire 805 has advanced out of distal tip 815 and thus, the length of the ACL. In another embodiment, a laser may be used to point to the femoral tunnel opening.

In yet another embodiment, a femoral offset guide arm may be used with an "acorn" reamer. An acorn reamer is a reamer having a shank that is smaller than its head. After drilling the tibial tunnel, the surgeon often uses an acorn reamer to form the femoral tunnel in the posterior region of the femoral notch. In this embodiment, the guide arm positions the tibial tunnel to ensure that the acorn reamer reaches the posterior region of the femoral notch.

The femoral offset guide arm also may be used to avoid impingement. Impingement occurs when the graft hits the femoral notch during extension of the knee. To avoid impingement, a three-dimensional representation of the graft is attached to the distal tip of the guide arm so that the surgeon can determine whether the graft will hit the femoral notch during extension of the knee.

There has been described novel and improved apparatus and techniques for positioning a tibial tunnel in ACL reconstruction. It is evident that those skilled in the art may now make numerous uses and modifications of and departures from the specific embodiments described herein without departing from the inventive concept.

What is claimed is:

1. A method for positioning a tunnel in a tibia, comprising:
   providing a guide including a guide arm having a rigid distal tip configured to contact a femoral surface, and a drill sleeve connected to the guide arm and having a distal tip configured to contact a tibial surface when the distal tip of the guide arm contacts the femoral surface; and
   positioning the guide in a patient's knee so that the distal tip of the drill sleeve contacts the tibial surface and the distal tip of the guide arm contacts the femoral surface.

2. The method in claim 1 further comprising:
   inserting a guidewire through the drill sleeve and drilling the guidewire through the tibia; and
   removing the guide from the patient's knee, leaving the guidewire in place to locate the tunnel.

3. The method of claim 1, wherein providing a guide comprises providing a handle connected between the guide arm and the drill sleeve such that the guide arm and the drill sleeve are connected through their connection to the handle.

4. The method of claim 3, wherein the guide arm and the drill sleeve are connected to the handle at opposite ends of the handle.

5. The method of claim 1, further comprising orienting the guide arm by adjusting the guide arm with respect to the drill sleeve, wherein the guide arm includes markings for indicating the orientation of the guide arm with respect to the drill sleeve.

6. The method of claim 1, further comprising measuring the length of the tibial tunnel, wherein the drill sleeve includes markings for measuring the length of the tibial tunnel.

7. The method of claim 1, wherein the distal tip of the drill sleeve includes an angled opening surrounded by teeth and positioning the guide in a patient's knee such that the distal tip of the drill sleeve contacts the tibial surface comprises pressing the teeth against the tibial surface.

8. The method of claim 1, wherein the distal tip of the guide arm includes a hook and positioning the guide in a patient's knee such that the distal tip of the guide arm contacts the femoral surface comprises contacting the hook against the femoral surface.

9. The method of claim 8, wherein the guide arm includes a spike and positioning the guide in a patient's knee such that the distal tip of the guide arm contacts the femoral surface further comprises contacting a spike against a tibial plateau.

10. The method of claim 1, wherein contacting the distal tip of the guide arm to the femoral surface comprises contacting the distal tip of the guide arm to the posterior cortex of the femoral notch.

11. The method of claim 1, further comprising using the guide to provide an offset from a point at which the distal tip of the guide arm contacts the femoral surface to a longitudinal axis of the drill sleeve, wherein the guide arm is configured to provide the offset.

12. The method of claim 1, wherein the guide arm includes a first distal arm portion having a hook and a second distal arm portion having a spike and contacting the distal tip of the guide arm against the femoral surface comprises contacting the femoral surface with the first distal arm portion of the guide arm while contacting the tibial plateau with the second distal arm portion of the guide arm.

13. The method of claim 1, further comprising using the guide to indicate isometry, wherein indicating isometry comprises indicating isometry between an opening of the tibial tunnel and an opening of a femoral tunnel.

14. The method of claim 13, wherein the guide further comprises a device for indicating isometry.

15. The method of claim 14, wherein the device comprises an isometry linkage.

16. The method of claim 15, further comprising extending the isometry linkage, wherein the guide includes means for extending the isometry linkage.

17. The method of claim 16, wherein the extending means comprises hydraulic means.

* * * * *